US008186873B1

(12) United States Patent
 Madding

(10) Patent No.: US 8,186,873 B1
(45) Date of Patent: May 29, 2012

(54) DETERMINATION OF THERMAL RESISTANCE USING INFRARED THERMOGRAPHY

(75) Inventor: Robert P. Madding, Carlisle, MA (US)

(73) Assignee: Flir Systems, Inc., Wilsonville, OR (US)

( * ) Notice: Subject to any disclaimer, the term of this patent is extended or adjusted under 35 U.S.C. 154(b) by 875 days.

(21) Appl. No.: 12/247,751

(22) Filed: Oct. 8, 2008

(51) Int. Cl.
 *G01N 25/20* (2006.01)
 *G01N 25/18* (2006.01)
 *G01J 5/00* (2006.01)

(52) U.S. Cl. ............ 374/43; 374/112; 374/121; 374/44; 702/136; 250/338.1

(58) Field of Classification Search ............... 374/43, 374/44, 120, 121, 124, 133, 135, 110, 112, 374/115, 29, 30, 4, 57, 137; 324/557, 559
See application file for complete search history.

(56) References Cited

U.S. PATENT DOCUMENTS

| | | | | |
|---|---|---|---|---|
| 4,236,403 A * | 12/1980 | Poppendiek | ..................... | 374/44 |
| 4,555,764 A * | 11/1985 | Kuehn | ........................... | 700/299 |
| 4,647,221 A * | 3/1987 | Szabo | ............................. | 374/44 |
| 5,115,967 A * | 5/1992 | Wedekind | ................... | 236/46 R |
| 5,877,688 A * | 3/1999 | Morinaka et al. | ............. | 340/584 |
| 7,034,300 B2 | 4/2006 | Hamrelius et al. | | |
| 7,748,197 B2 * | 7/2010 | Romes et al. | ................ | 52/794.1 |
| 7,851,758 B1 * | 12/2010 | Scanlon et al. | ............... | 250/330 |
| 2002/0116239 A1 * | 8/2002 | Reinsma et al. | ................... | 705/7 |
| 2009/0304042 A1 * | 12/2009 | Agronin | ........................ | 374/112 |

OTHER PUBLICATIONS

Standard Practice for Determining Thermal Resistance of Building Envelope Components from the In-Situ Data, ASTM International, Designation: C 1155 -95, May 2007, 8 pages.
Standard Practice for In-Situ Measurement of Heat Flux and Temperature on Building Envelope Components, ASTM International, Designation: C 1046—95, May 2007, 9 pages.
Application of Infrared Sensing Devices to the Assessment of Building Heat Loss Characteristics, ANSI/ASHRAE 101-1981, The American Society of Heating, Refrigerating, and Air-Conditioning Engineers, Inc., 1983, 33 pages.
Cheeseman et al., Developing An In-Situ Post-Construction Quality Control Methodology to Ensure Better Energy Efficiency of Buildings, Proceedings of the 10th International Conference on Environmental Science and Technology, Sep. 5-7, 2007, pp. A-228-A-235.
D.W.J. Hamoen, New low-cost residential energy audit technique, Thermal Energy Devices, SPIE vol. 313 Thermosense IV, 1981, pp. 35-44.
Flanders et al., Interpolating R-values from thermograms, U.S. Army Cold Regions Research and Engineering Laboratory, SPIE vol. 313 Thermosense IV, 1981, pp. 157-164.
R-value (insulation)—Wikipedia, the free encyclopedia, http://en.wikipedia.org/wiki/R-value_(insulation), Sep. 4, 2008, 6 pages.
Thermodynamic equilibrium—Wikipedia, the free encyclopedia, http://en.wikipedia.org/wiki/Thermal_equilibrium, Oct. 8, 2008, 3 pages. Thermal insulation—Building elements—In-situ measurement of thermal resistance and thermal transmittance—Part 2: Infrared method, ISO/TC 163/SC 1 N 000, May 30, 2008, 31 pages.

* cited by examiner

*Primary Examiner* — Amy Cohen Johnson
(74) *Attorney, Agent, or Firm* — Haynes and Boone, LLP

(57) ABSTRACT

Various techniques are provided for determining thermal resistance values of building materials through the use of infrared cameras. In one example, an infrared camera may be used to capture one or more infrared images of a wall. Using temperatures obtained from the images, a thermal resistance value such as an R-Value associated with the wall may be determined. Potential cost savings associated with adjusting the thermal resistance value may also be determined.

38 Claims, 7 Drawing Sheets

US 8,186,873 B1

DETERMINATION OF THERMAL RESISTANCE USING INFRARED THERMOGRAPHY

BACKGROUND

1. Field of the Invention

The present invention generally relates to infrared measurement techniques, and more particularly to the use of infrared cameras to determine attributes of building materials.

2. Related Art

As is well known, R-Values can be used to identify the resistance to heat flow exhibited by building materials. For example, insulation or other building materials may be rated by R-Values (for example, R-13, R-19, or other values), wherein higher R-Values indicate better insulation performance. In the United States, R-Values are generally expressed in English units: $F*ft^2*Hour/BTU$. By dividing English R-Values by 5.673, the R-Values can be expressed in metric units: $C*m^2/W$. In various applications, insulation performance may be identified by the reciprocal of R-Value, called U-Value: $U=1/R$.

Unfortunately, after insulation or other building materials are installed in a wall of a structure, it is often difficult to ascertain the effective R-Value exhibited by the wall. For example, after insulation is installed, it is typically hidden from view. As a result, it may be difficult to determine the actual R-Value of the insulation without at least partially damaging the wall. Moreover, because the wall's overall resistance to heat flow may depend on other wall components (e.g., drywall, siding, and/or other materials), knowing the R-Value of insulation in the wall will not necessarily provide an accurate indication of the overall R-Value exhibited by the wall. Accordingly, there is a need for an improved approach to the determination of R-Values that overcomes some or all of the deficiencies discussed above.

SUMMARY

Various techniques are provided for determining R-Values of building materials through the use of infrared cameras. For example, an infrared camera may be used to capture one or more infrared images of a wall. Using temperatures obtained from the images, an R-Value associated with the wall may be determined. Potential cost savings associated with adjusting the R-Value may also be determined.

In one embodiment, a method of determining thermal resistance associated with a wall includes capturing an infrared image comprising a surface of the wall and a surface of at least one target using an infrared camera, wherein the wall surface and the target are in a first environment on a first side of the wall; determining a temperature of the wall surface from the infrared image; determining a temperature of the target surface from the infrared image; determining a temperature of a second environment on a second side of the wall; and calculating a thermal resistance value of the wall based on the wall surface temperature, the target surface temperature, and the temperature of the second environment.

In another embodiment, a system for determining thermal resistance associated with a wall includes an infrared camera adapted to: capture an infrared image comprising a surface of the wall and a surface of at least one target, wherein the wall surface and the target are in a first environment on a first side of the wall, determine a temperature of the wall surface from the infrared image, and determine a temperature of the target surface from the infrared image; and a processor configured to calculate a thermal resistance value of the wall based on the wall surface temperature, the target surface temperature, and a temperature of a second environment on a second side of the wall.

In another embodiment, a machine-readable medium includes a plurality of machine-readable instructions which when executed by a device are adapted to cause the device to perform a method of determining thermal resistance associated with a wall, the method includes instructing a user to operate an infrared camera to capture an infrared image comprising a surface of the wall and a surface of at least one target, wherein the wall surface and the target are in a first environment on a first side of the wall; instructing a user to measure a temperature of a second environment on a second side of the wall; determining a temperature of the wall surface from the infrared image; determining a temperature of the target surface from the infrared image; and calculating a thermal resistance value of the wall based on the wall surface temperature, the target surface temperature, and the temperature of the second environment.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE FIGURES

Embodiments of the present invention and their advantages are best understood by referring to the detailed description that follows. It should be appreciated that like reference numerals are used to identify like elements illustrated in one or more of the figures.

DETAILED DESCRIPTION

Various techniques are provided for determining thermal resistance values of building materials through the use of infrared cameras. For example, in one embodiment, an infrared camera may be used to capture one or more infrared images of a wall. Using temperatures obtained from the images, a thermal resistance value associated with the wall may be determined. Potential cost savings associated with adjusting the thermal resistance value may also be determined. Although thermal resistance values will be described herein with regard to R-Values in English units, it will be appreciated that the various techniques described herein may be similarly used to determine other thermal resistance values such as R-Values expressed in metric units, U-Values, and/or other values where appropriate. When referring to temperature differences, it will also be appreciated that degrees Rankine and Kelvin may be substituted for degrees Fahrenheit and Celsius where appropriate.

Figure 1:
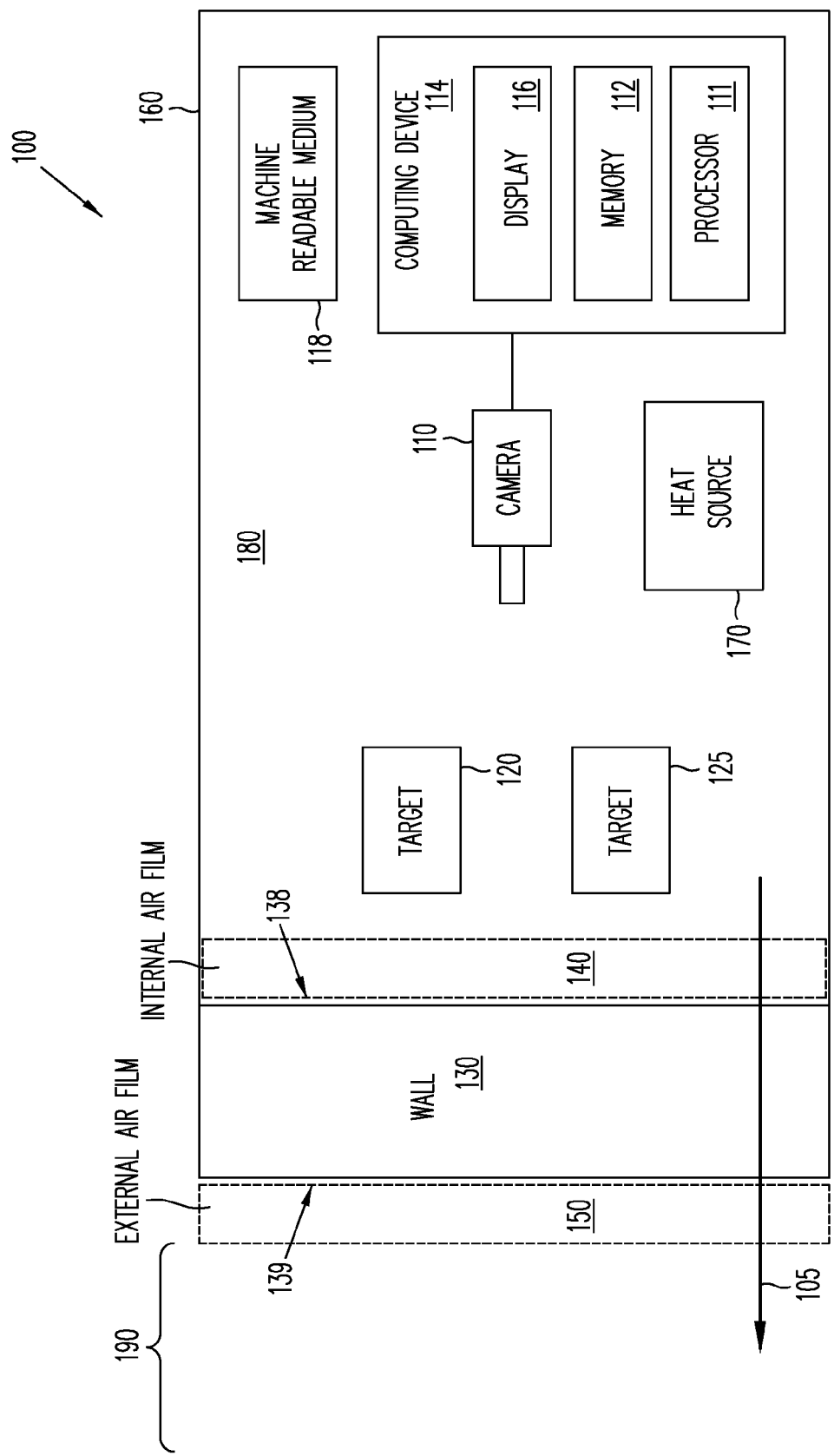
FIG. 1 illustrates a system for determining an R-Value of a wall in accordance with an embodiment of the invention.

Referring now to the drawings wherein the showings are for purposes of illustrating embodiments of the present invention only, and not for purposes of limiting the same, FIG. 1 illustrates a system 100 for determining an R-Value of a wall 130 in accordance with an embodiment of the invention. As shown in FIG. 1, a structure 160 has a wall 130 that separates one environment 180 (e.g., an indoor environment) from another environment 190 (e.g., an outdoor environment). In this regard, it will be appreciated that although environments 180 and 190 are described herein as indoor and outdoor environments, respectively, various embodiments of the invention may be applied to other combinations of environments (e.g., two indoor environments, two outdoor environments, or other combinations).

An R-Value of wall 130 may be determined in accordance with various techniques described herein. For example, in one embodiment, an R-Value of wall 130 may be determined when environments 180 and 190 exhibit a temperature difference and heat transfer between environments 180 and 190 approaches a substantially steady state condition. In this regard, as the temperature difference between environments 180 and 190 increases, the accuracy of the R-Value also increases. Also, as heat transfer between environments 180 and 190 more closely approximates a steady state condition, the accuracy of the R-Value increases. In one example, an R-Value may be determined when the temperature difference between environments 180 and 190 is preferably approximately 18 degrees F. (10 degrees C.) or greater and substantially steady state heat transfer conditions exist. In another embodiment, an R-Value may be determined with reduced accuracy when other temperature differences (e.g., larger or smaller temperature differences) and/or other heat transfer conditions (e.g., quasi-steady state conditions) exist.

A camera 110 is positioned in environment 180 to capture images of wall 130. For example, camera 110 may be implemented as an infrared camera configured to capture infrared images of a surface 138 of wall 130 facing environment 180. In certain embodiments, camera 110 may be implemented as a P640 infrared camera, a P65HS infrared camera, or a P65HSV infrared camera available from FLIR Systems, Inc. of Boston, Mass. In other embodiments, any type of infrared camera may be used.

In order to reduce the effects of random errors in infrared images captured by camera 110, it is preferable that camera 110 has a low noise equivalent temperature difference (NETD). For example, in one embodiment, camera 110 may be configured to exhibit a NETD of approximately 40 mK or lower.

In one embodiment, camera 110 may be configured with appropriate hardware and/or software to perform various calculations further described herein and/or to provide user interfaces as also further described herein. In another embodiment, camera 110 may be in communication with a computing device 114 which performs such calculations and/or provides such user interfaces.

As shown in FIG. 1, computing device 114 includes a processor 111, a memory 112, and a display 116. Processor 111 may be configured with appropriate software (e.g., a computer program for execution by a computer) that is stored on machine readable medium 118 and/or in memory 114 to instruct processor 111 to perform one or more of the operations described herein. In one embodiment, the software may be implemented as a Microsoft Excel file including appropriate Visual Basic code to perform such operations available from FLIR Systems, Inc. Display 116 may be used to provide appropriate user interfaces described herein. In another embodiment, processor 111, memory 112, display 116, and/or computing device 114 may be implemented in camera 110.

Targets 120 and 125 are also in the field of view of camera 110. As such, images captured by camera 110 may include surface 138, target 120, and target 125. In one embodiment, each of targets 120 and 125 may be positioned near wall surface 138 (e.g., within approximately 18 inches of wall surface 138).

Target 120 may be implemented as a substantially reflective target which, when captured in an infrared image by camera 110, can be used to determine a reflected apparent temperature of environment 180. For example, in one embodiment, target 120 may be implemented with an aluminum foil surface or other appropriate reflective surface facing camera 110. In one embodiment, the reflected apparent temperature determined from the surface of target 120 is approximately an average temperature of all surfaces in environment 180.

In another embodiment, the average temperature of all surfaces in environment 180 may be determined by capturing an infrared image using camera 110 when camera 110 is positioned near wall 130 and facing away from surface 138. In this regard, the overall temperature of the infrared image (e.g., taken with camera 110 facing toward the center of environment 180) may be used to approximate the average temperature of all surfaces in environment.

Target 125 may be implemented as a substantially non-reflective target which, when captured in an infrared image by camera 110, can be used to determine a temperature of the air of environment 180. For example, in one embodiment, target 125 may be implemented with a paper or cardboard surface facing camera 110.

In the embodiment illustrated in FIG. 1, camera 110, target 120, and target 125 are shown positioned in environment 180. However, in another embodiment, camera 110, target 120, and/or target 125 (or a different camera or targets) may be positioned in environment 190 to capture additional images if desired. For example, camera 110 may be used to capture infrared images of a surface 139 of wall 130 facing environment 190. Targets 120 and/or 125 may also be placed in the field of view of camera 110 in environment 190 as similarly described herein with regard to environment 180. As such, images captured by camera 110 in this case may include surface 139 of wall 130, target 120, and target 125.

Various temperatures can be obtained from the infrared images captured by camera 110 of wall surface 138, wall surface 139, target 120, and target 125 in environments 180 and 190. For example, in one embodiment, wall surface temperatures Twall1 and Twall2 associated with wall surfaces 138 and 139, respectively, can be determined from such infrared images. Air temperatures Tair1 and Tair2 associated with environments 180 and 190, respectively, can be determined from infrared images of target 125 placed in such environments.

In addition, reflected apparent temperatures Trat1 and Trat2 associated with environments 180 and 190, respectively, can be determined from infrared images of target 120 placed in such environments. In one embodiment, it is assumed that all surfaces other than wall surface 138 in infrared images captured by camera 110 in indoor environments (e.g., in environment 180) exhibit reflected apparent temperature Trat1 (e.g., a unity view factor is assumed for indoor environments). Also in this embodiment, a unity view factor is not assumed for outdoor environments (e.g., in environment 190).

FIG. 1 also shows an arrow 105 which denotes heat flow from environment 180 to environment 190 through wall 130. In this regard, a heat source 170 is also shown in environment 180. Heat source 170 may be any type of heat source such as, for example, a heating system for structure 160, human bodies, or other heat sources. In particular, the introduction of one or more human bodies in environment 180 may prevent steady state heat flow conditions from being realized for a period of time (e.g., approximately two hours). Therefore, in one embodiment, it is preferable that no human bodies are present in environment when thermal images are captured by camera 110. In another embodiment, a cooling source (for example, in environment 190) may cause the heat flow denoted by arrow 105. Although arrow 105 is directed from environment 180 to environment 190, it will be appreciated that heat flow in the opposite direction (e.g., from environment 190 to environment 180 by an appropriate heat source in environment 190 and/or a cooling source such as an air conditioning system for structure 160 in environment 180) may be present in other embodiments.

As shown in FIG. 1, heat flowing from environment 180 to environment 190 (e.g., denoted by arrow 105) passes through an internal air film 140 adjacent to surface 138 of wall 130 in environment 180, and an external air film 140 adjacent to surface 139 of wall 130 in environment 190 as will be further described herein.

Figure 2:
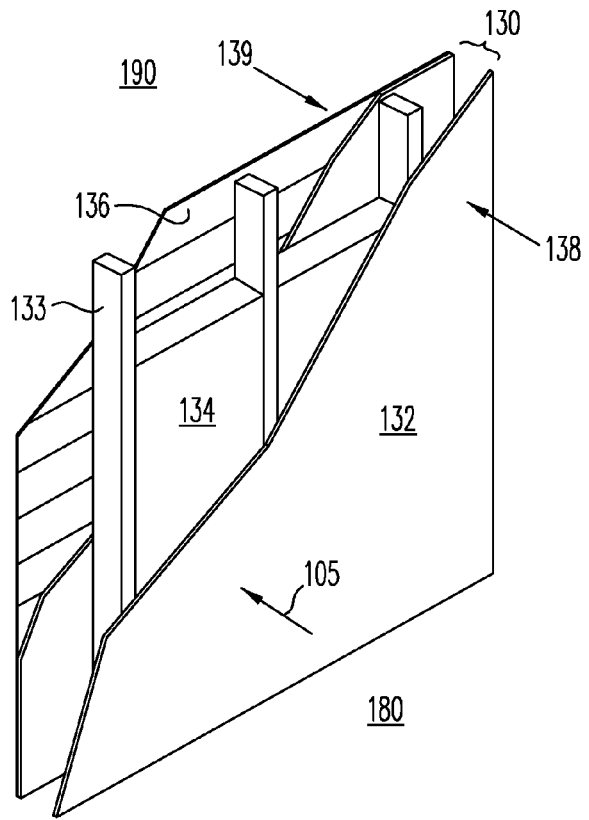
FIG. 2 illustrates a cutaway view of the wall of FIG. 1 in accordance with an embodiment of the invention.

FIG. 2 illustrates a cutaway view of wall 130 in accordance with an embodiment of the invention. Wall 130 may be implemented as an external wall of structure 160 using conventional stud frame wall construction with insulated wall cavities. For example, as shown in FIG. 2, wall 130 may include studs 133 (e.g., wood or metal studs), insulation 134, drywall 132, and siding 136. As also shown in FIG. 2, drywall 132 provides surface 138 facing environment 180, and siding 136 provides surface 139 facing environment 190.

Figure 3:
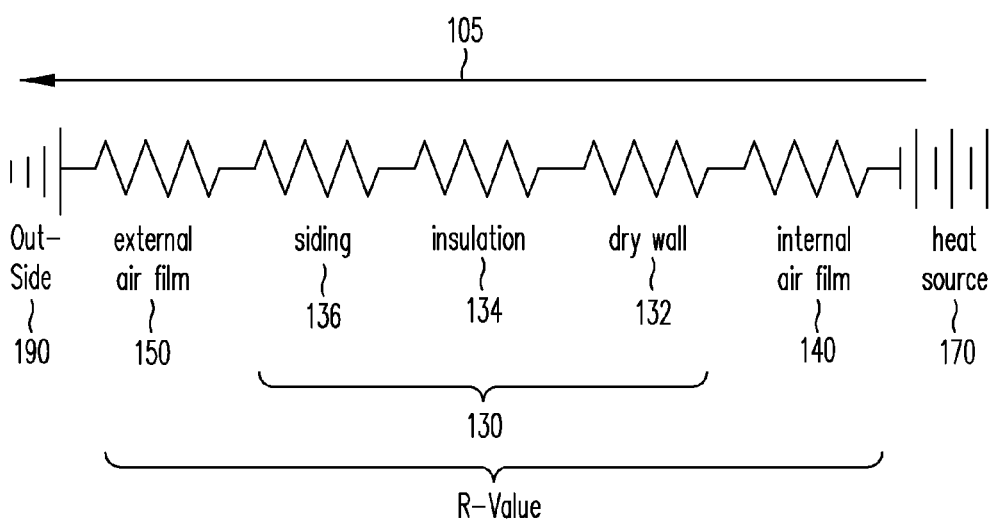
FIG. 3 illustrates a conceptual representation of the wall of FIG. 1 in accordance with an embodiment of the invention.

FIG. 3 illustrates a conceptual representation of wall 130 in accordance with an embodiment of the invention. In this regard, the steady state heat flow in FIGS. 1 and 2 is conceptually represented by a series of thermal resistors connected between heat source 170 and environment 190. In the conceptual representation shown in FIG. 3, outside environment 190 acts as a heat sink represented by a ground.

Internal air film 140, wall 130, and external air film 150 reduce the heat flow from heat source 170 (represented by a battery in FIG. 3) to environment 190 in accordance with an R-Value that is associated with the combination of internal air film 140, wall 130, and external air film 150. For steady state conductive heat flow in the direction of arrow 105 in FIGS. 1-3, the R-Value associated with wall 130 (e.g., corresponding to the combination of internal air film 140, wall 130, and external air film 150 in one embodiment) is given by the following equation 1, where A is the surface area of wall 130 that heat Q is flowing through driven by $\Delta T_{io}$ which is the difference between temperature Tair1 of environment 180 and temperature Tair2 of environment 190:

$$R - \text{Value} = \frac{A \Delta T_{io}}{Q} \quad \text{(equation 1)}$$

In one embodiment, camera 110 may include a distance meter (e.g., range finder) such as laser range finder which may be used to determine the distance from camera 110 to wall 130. An example of an infrared camera incorporating a distance meter is provided by U.S. Pat. No. 7,034,300 which is incorporated herein by reference in its entirety. Based on the distance from camera 110 to wall 130 provided by the distance meter, camera 110 and/or computing device 114 may be configured to calculate the surface area A of wall 130. The calculated surface area A may be used by camera 110 and/or computing device 114 in accordance with the various equations described herein. In another embodiment, camera 110 and/or computing device 114 may be configured to calculate the surface area A of wall 130 based on the distance from camera 110 to wall 130 provided by a user. Advantageously, a laser projected on wall 130 by a laser range finder may permit a user to visually identify portions of wall 130 and match such portions to infrared images of wall 130.

Steady state heat flow through internal air film 140 is by radiation and convection. Regarding radiation, the steady state radiative heat transfer through internal air film 140 can be determined by the following equation 2, where $\epsilon_{wall}$ is the emissivity of wall surface 138 (e.g., which may be assumed to be the same for surfaces in one embodiment), $\sigma$ is the Stefan Boltzmann constant, A is the area of wall surface 138, $F_{12}$ is the view factor, $T_{wall}$ is the wall temperature in absolute units, and $T_{rat}$ is the reflected apparent temperature in absolute units (e.g., Kelvin or Rankine):

$$Q_{rad} = \sigma \epsilon_{wall} A F_{12} (T_{wall}^4 - T_{rat}^4) \quad \text{(equation 2)}$$

The steady state radiative heat transfer of equation 2 can be approximated by the following equation 3, where $T_m$ is the absolute average (e.g., mean) of the temperature Twall1 of wall surface 138 and the reflected apparent temperature Trat1 of target 120, $\Delta Tr$ is the difference between the temperature Twall1 of wall surface 138 and the reflected apparent temperature Trat1 of target 120, and the view factor is assumed to be 1:

$$Q_{rad} = 4 \sigma \epsilon_{wall} A T_m^3 \cdot \Delta T_r \quad \text{(equation 3)}$$

In various embodiments, either or both of equations 2 and 3 may be used. For example, in one embodiment, equation 3 may be used for calculating radiative heat transfer to determine R-Values and equation 2 may be used for uncertainty analysis performed on the calculated R-Values.

Heat transfer by convection is given by the following equation 4, where $h_c$ is the convective coefficient, A is the surface area of wall 130 that convective heat Qconv is flowing through, and $\Delta Ta$ is the difference between the temperature Twall1 of wall surface 138 and the temperature Tair1 of environment 180:

$$Q_{conv} = h_c A \Delta T_a \quad \text{(equation 4)}$$

The value of convective coefficient $h_c$ can be calculated for laminar flows or turbulent flows as may be desired for particular applications. For example, in one embodiment, turbulent flow values of convective coefficient $h_c$ are preferred where tall walls and large differences between wall temperatures and air temperatures are present.

In one embodiment, convective coefficient $h_c$ can be calculated for laminar flows using the following equation 5, where L is the characteristic length in feet (e.g., a height of wall 130). In one embodiment, L is assumed to be approximately 1 meter. In other embodiments, L corresponds to an actual measured height of wall 130.

$$h_c = 0.25\left(\frac{\Delta T_a}{L}\right)^{\frac{1}{4}} \text{ in BTU/(Hour} * \text{ft}^2 * \text{F.)} \quad \text{(equation 5)}$$

In another embodiment, convective coefficient $h_c$ can be calculated for laminar flows using the following equation 6:

$$h_c = 0.23\left(\frac{\Delta T_a}{L}\right)^{\frac{1}{4}} \text{ in BTU/(Hour} * \text{ft}^2 * \text{F.)} \quad \text{(equation 6)}$$

Equations 5 and 6 can be expressed in metric units as set forth in the following equations 7 and 8, respectively:

$$h_c = 1.42\left(\frac{\Delta T_a}{L}\right)^{\frac{1}{4}} \text{ in Watt/(m}^2 * \text{C.)} \quad \text{(equation 7)}$$

$$h_c = 1.31\left(\frac{\Delta T_a}{L}\right)^{\frac{1}{4}} \text{ in Watt/(m}^2 * \text{C.)} \quad \text{(equation 8)}$$

In another embodiment, convective coefficient $h_c$ can be calculated for turbulent flows using the following equation 9:

$$h_c = 0.23(\Delta T_a)^{1/3} \text{ in BTU/(Hour*ft}^2*F) \quad \text{(equation 9)}$$

In another embodiment, convective coefficient $h_c$ can be calculated for turbulent flows using the following equation 10:

$$h_c = 0.317(\Delta T_a)^{1/4} \text{ in BTU/(Hour*ft}^2*F) \quad \text{(equation 10)}$$

Equations 9 and 10 can be expressed in metric units as set forth in the following equations 11 and 12, respectively:

$$h_c = 1.31(\Delta T_a)^{1/3} \text{ in Watt/}(m^2*C) \quad \text{(equation 11)}$$

$$h_c = 1.8(\Delta T_a)^{1/4} \text{ in Watt/}(m^2*C) \quad \text{(equation 12)}$$

Substituting the radiant and convective heat values Qrad and Qconv of equations 3 and 4 into equation 1 provides the following equation 13 with known constants and measurable variables:

$$R-\text{Value} = \frac{\Delta T_{io}}{4\varepsilon\sigma T_m^3 \Delta T_r + h_c \Delta T_a} \quad \text{(equation 13)}$$

Thus, it will be appreciated that the R-Value of a desired medium may be determined by measuring or otherwise determining the values set forth in equation 13. In particular, by measuring particular temperature values using camera 110 of FIG. 1, the R-Value associated with wall 130 can be determined.

Figure 4:
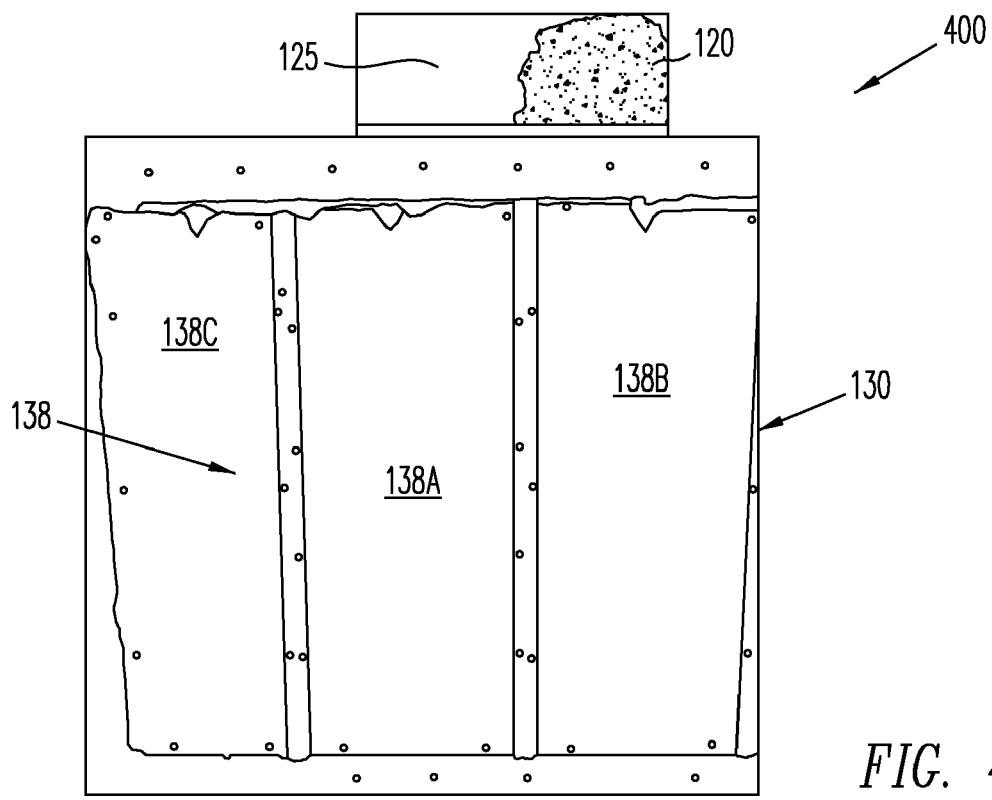
FIG. 4 illustrates an example of a photographic image of the wall of FIG. 1 in accordance with an embodiment of the invention.

FIG. 4 illustrates an example of a photographic image 400 of wall 130 taken, for example, by camera 110 in environment 180 in accordance with an embodiment of the invention. In the example shown in FIG. 4, wall 130 is constructed of conventional drywall and ½ inch plywood. Wall surface 138 includes areas 138A-C. Insulation 134 of wall 130 (shown in FIG. 2) may be implemented with different types of insulating materials behind each of areas 138A-C. For example, wall 130 may be filled with dense packed cellulose behind area 138A, loose fill cellulose behind area 138B, and crumpled newspaper behind area 138C. As also shown in FIG. 4, targets 120 and 125 are in proximity to wall 130 and are captured with wall 130 in image 400.

Figure 5:
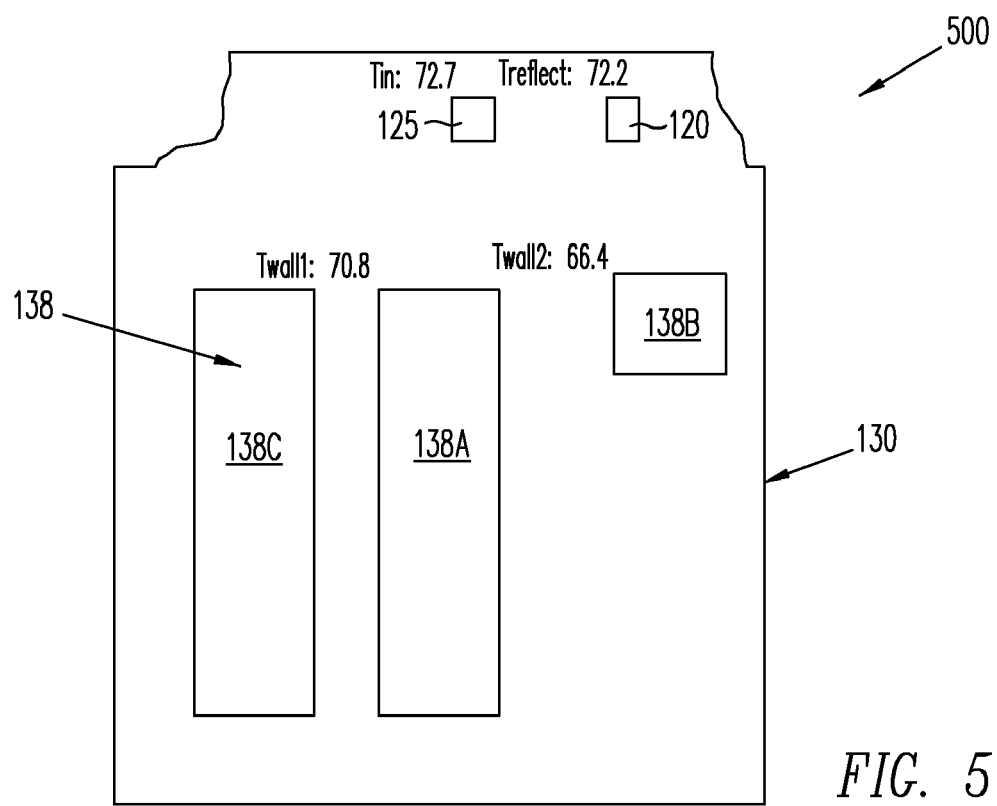
FIG. 5 illustrates an example of an infrared image of the wall of FIG. 1 in accordance with an embodiment of the invention.

FIG. 5 illustrates an example of an infrared image 500 of wall 130 taken, for example, by camera 110 from the same perspective as FIG. 4 in environment 180 in accordance with an embodiment of the invention. Dark areas in areas 138A-C in image 500 indicate cold spots that are characteristic of inadequate insulation. For example, as shown in FIG. 5, the loose fill cellulose behind area 138B has settled significantly, leaving an uninsulated gap behind a top portion of area 138B.

Using infrared image 500, camera 110 and/or computing device 114 may determine various temperatures associated with various areas of wall 130 and targets 120 and 125 captured in image 500. For example, as also shown in FIG. 5, area 138A has a measured temperature of 70.6 degrees F. and area 138B has a measured temperature of 66.4 degrees F. Either or both of these temperatures may be used, for example, as wall surface temperature Twall1 in the equations described herein. Target 120 has a measured temperature of 72.2 degrees F. which may be used, for example, as reflected apparent temperature Trat1 in the equations described herein. Target 125 has a measured temperature of 72.7 degrees F. which may be used, for example, as air temperature Tair1 in the equations described herein.

It will be appreciated that other temperatures Twall2, Trat2, and Tair2 may be measured by taking a similar infrared image of the other side of wall 130 from camera 110 (or another camera) in environment 190 facing wall surface 139 in accordance with an embodiment of the invention. By capturing infrared images of different sides of wall 130, appropriate temperature values may be measured which may be applied to equation 13 for determining an R-Value associated with wall 130.

Figure 6:
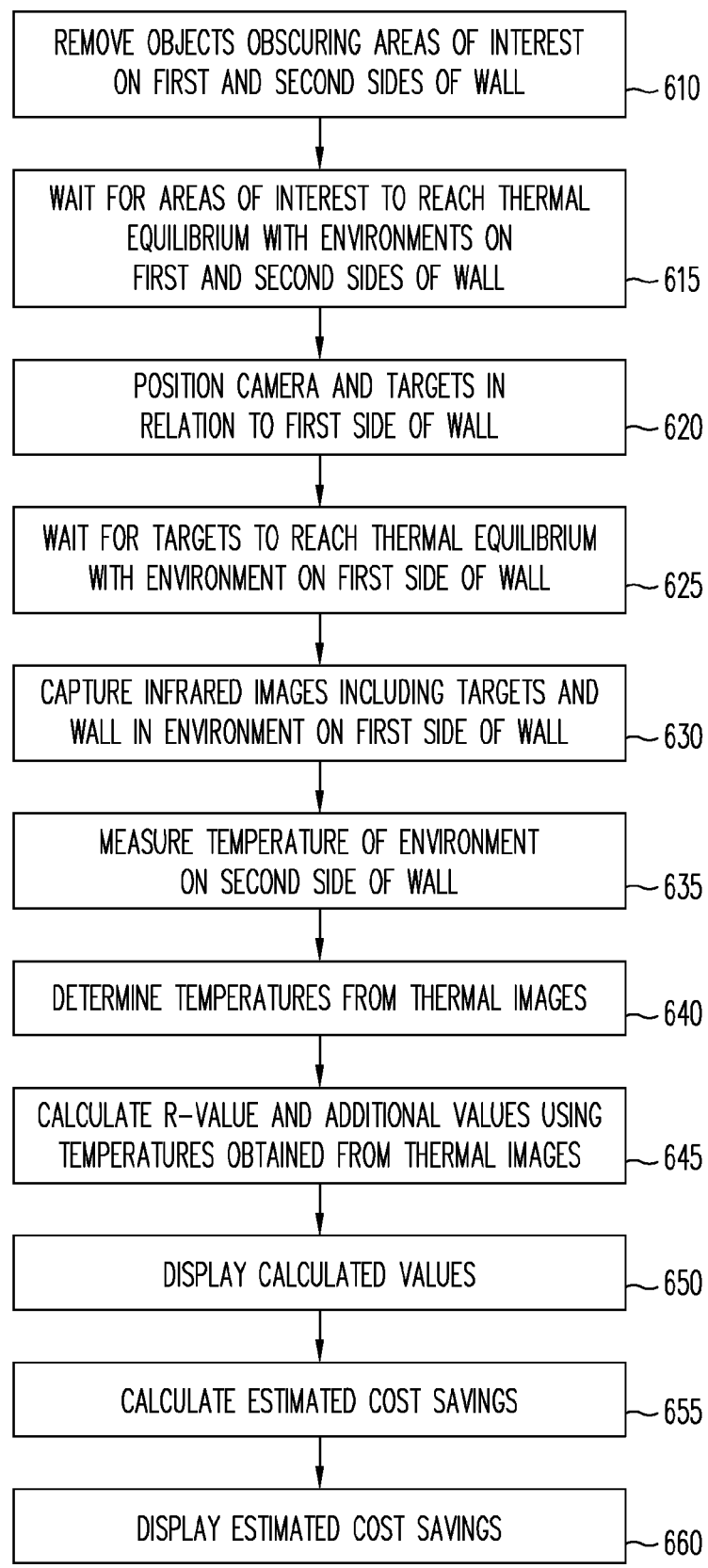
FIG. 6 illustrates a process of determining an R-Value of the wall of FIG. 1 in accordance with an embodiment of the invention.
Figure 7:
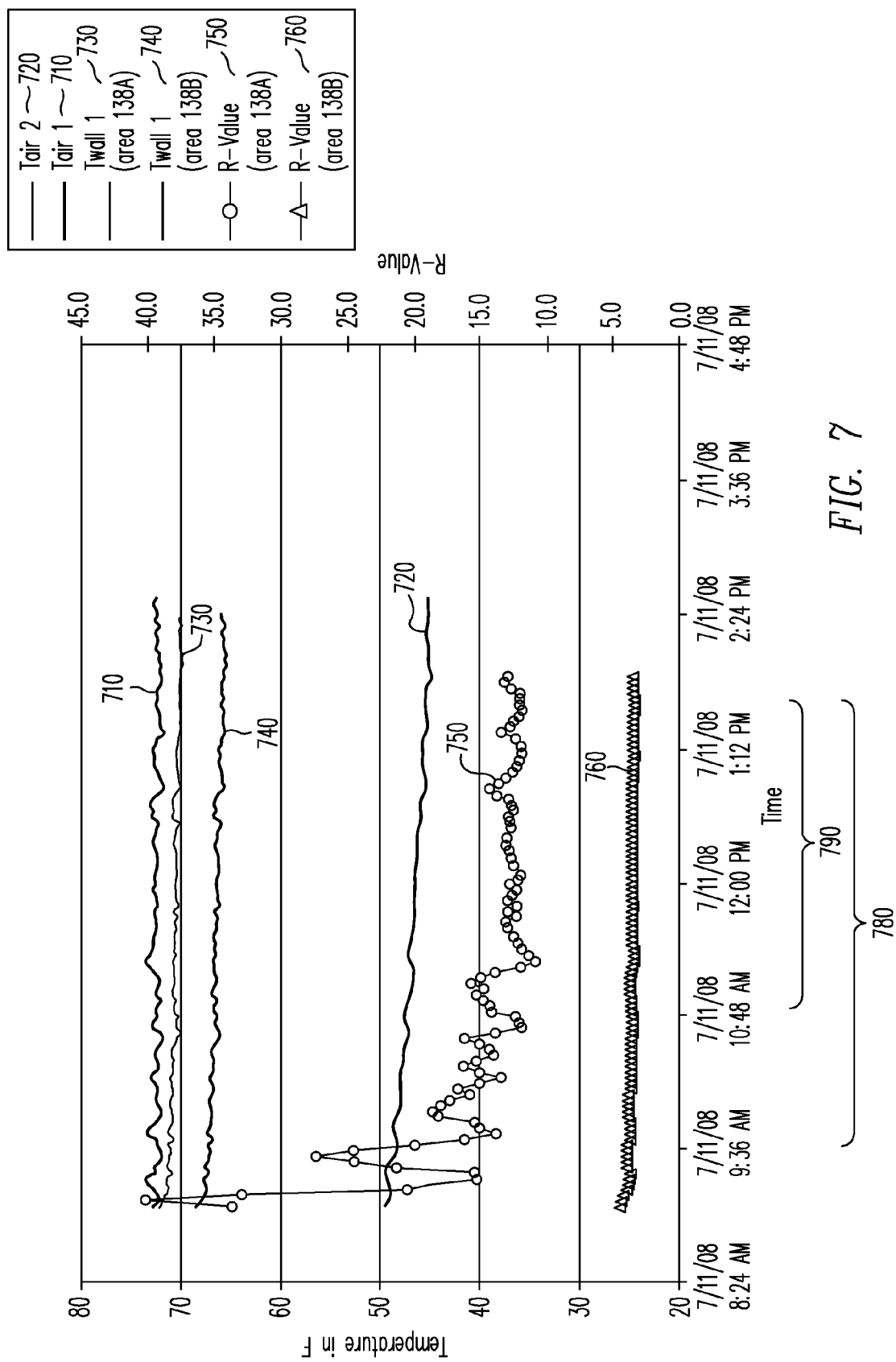
FIG. 7 illustrates an example of a data set obtained during the process of FIG. 6 in accordance with an embodiment of the invention.

FIG. 6 illustrates a process of obtaining temperature measurements of wall 130 in accordance with an embodiment of the invention. For example, in one embodiment, the process of FIG. 6 may be performed by a user interacting with camera 110, computing device 114, targets 120/125, and/or other appropriate equipment. In another embodiment, camera 110 and/or computing device 114 may be configured to instruct the user to perform appropriate steps of the process of FIG. 6 through a user interface. In another embodiment, camera 110 and/or computing device 114 may be configured to perform appropriate steps of the process of FIG. 6 in response to machine-readable instructions (e.g., which may be provided by machine readable medium 118) executed by a processor 111 of computing device 114 and/or executed by camera 110. FIG. 7 illustrates an example of a data set obtained during the process of FIG. 6 in accordance with an embodiment of the invention, as will be further described herein.

Referring now to the steps of the process of FIG. 6, in step 610, objects that may obscure areas of interest on wall surfaces 138 and 139 are removed. For example, it will be appreciated that pictures, furniture, clocks, or other objects that preclude a direct view of areas of interest on wall surfaces 138 and 139 may affect heat flow through wall 130 and alter R-Values determined for portions of wall 130 that are directly behind such objects. Accordingly, in one embodiment, step 610 may be performed if any objects obscure areas of interest for which a user desires to determine an R-Value. However, in another embodiment, step 610 may be omitted if areas of interest are not obscured by such objects. In another embodiment, step 610 is not performed for wall surfaces facing an outside environment.

In step 615, any areas of interest on wall surfaces 138 and 139 that have been recently exposed to environments 180 and 190 (for example, as a result of removing objects in previous step 610), are permitted to substantially reach thermal equilibrium (i.e., having a temperature that does not change substantially over time) with environments 180 and 190. In one embodiment, step 615 is not performed for wall surfaces facing an outside environment (e.g., if previous step 610 has not been performed for such wall surfaces).

In step 620, camera 110, target 120, and target 125 are positioned within environment 180. For example, target 120 and target 125 may be positioned in the field of view of camera 110 and in front of wall surface 138 such that infrared images captured by camera 110 include wall surface 138 and targets 120 and 125 as shown in FIG. 1.

In step 625, targets 120 and 125 are permitted to substantially reach thermal equilibrium with environment 180 (i.e., having approximately the same temperature as the air in environment 180). For example, if targets 120 and 125 are introduced into environment 180 from another environment (e.g., environment 190 which may be at a substantially lower temperature), then infrared images of targets 120 and 125 may not accurately indicate reflected apparent temperature Trat1 and air temperature Tair1 of environment 180. Thus, permitting targets 120 and 125 reach thermal equilibrium with environment 180 can improve the accuracy of temperature values determined from such infrared images.

In step 630, camera 110 captures one or more infrared images of wall surface 138, target 120, and target 125. In order to improve the accuracy of such infrared images, it is preferable that a user's body heat does not interfere with the infrared images. In this regard, it is preferable that a user is not positioned near camera 110, wall 130, target 120, target 125, or portions of environment 180 in a manner that may affect the infrared images.

In one embodiment, step 630 may be repeated to obtain any desired number of infrared images over a period of time. For example, step 630 may be repeated at desired intervals to capture different infrared images associated with different times of day or night. For example, in one embodiment, camera 110 may capture infrared images approximately every 30 seconds for a desired time period. As a result, changes in temperature due to solar loading, wind, weather, or other factors may be observed. In this regard, in certain embodiments, it is preferable to use infrared images taken during times in which heat flow 105 exhibits a substantially steady state condition. By observing changes in temperature during a desired time period, infrared images taken during substantially steady state conditions can be identified and used for further temperature calculations. For example, in one embodiment, camera 110 and/or computing device 114 may be configured to identify (e.g., select) such temperatures.

In another embodiment, step 630 may be repeated for different areas of interest of wall surface 138. For example, different infrared images may be captured for different areas 138A, 138B, or 138C of wall surface 138. In this regard, camera 110, target 120, and/or target 125 may be repositioned as desired during step 630 to appropriately capture such areas of interest.

It will be appreciated that, as a result of step 630, one or more infrared images of wall surface 138, target 120, and target 125 will be obtained. Using these infrared images, camera 110 and/or computing device 114 may determine temperatures, such as wall surface temperature Twall1, reflected apparent temperature Trat1, and air temperature Tair1 described herein. In one embodiment, an emissivity value of 1.0 may be used for determining reflected apparent temperature Trat1, and an emissivity value of 0.95 may be used for determining wall surface temperature Twall1 and air temperature Tair1.

In step 635, a temperature of environment 190 (e.g., corresponding to Tair2) is measured. In one embodiment, step 635 is performed following step 630 as shown in FIG. 6. In another embodiment, step 635 may be performed substantially simultaneously with previous steps 620, 625, and 630.

It will be appreciated that the temperature values described herein may be measured in a variety of ways. For example, in one embodiment, the air temperature Tair2 of environment 190 may be measured in step 635 by an appropriate temperature sensor, weather station, thermometer, or other appropriate measuring device positioned in environment 190. Thus, in such an embodiment, an infrared image need not be taken from environment 190. As a result, a user may remain inside structure 160 in environment 180 without having to capture thermal images outdoors.

In another embodiment, one or more thermal images may be captured in environment 190 and used by camera 110 and/or computing device 114 to determine temperatures, such as wall surface temperature Twall2, reflected apparent temperature Trat2, and air temperature Tair2 described herein. For example, in one embodiment, the air temperature Tair2 of environment 190 may be determined from a thermal image of target 125 captured while target 125 is positioned in environment 190 and is substantially at thermal equilibrium with environment 190.

Preferably, only one camera (e.g., camera 110) is used to capture all infrared images during the process of FIG. 6. In this regard, by using the same camera to capture all infrared images, any systematic errors exhibited by camera 110 will nevertheless be consistently applied to all of the infrared images. As a result, the effects of systematic errors in the calculations performed in subsequent steps can be greatly reduced.

In step 640, camera 110 and/or computing device 114 determines temperature values based on the infrared images captured in step 630 and/or step 635. In various embodiments, such temperature values may include one or more of the following temperature values: wall surface temperatures Twall1/Twall2, reflected apparent temperatures Trat1/Trat2, and/or air temperatures Tair1/Tair2 described herein.

FIG. 7 illustrates several types of temperature values determined in step 640 from a set of infrared images. In this regard, plot 710 shows temperatures determined for air temperature Tair1 of environment 180, plot 720 shows temperatures determined for air temperature Tair2 of environment 190, plot 730 shows temperatures determined for wall surface temperature Twall1 for area 138A of wall surface 138, and plot 740 shows temperatures determined for wall surface temperature Twall1 for area 138B of wall surface 138.

In some embodiments, air temperature values Tair1 and Tair2 may be approximately equal to reflected apparent temperatures Trat1 and Trat2, respectively. In such embodiments, air temperature values Tair1 and Tair2 may be substituted for reflected apparent temperatures Trat1 and Trat2, or vice versa, thus reducing the number of temperature measurements to be performed. Accordingly, for the plots shown in FIG. 7, it is assumed that air temperature values Tair1 and Tair2 are approximately equal to reflected apparent temperatures Trat1 and Trat2. As such, reflected apparent temperatures Trat1 and Trat2 are not shown in FIG. 7. In step 645, camera 110 and/or computing device 114 calculates an R-Value associated with wall 130 based on the temperature values determined in previous step 640. For example, step 645 may be performed by applying appropriate values into equation 13 described herein.

FIG. 7 further illustrates various R-Values determined in step 645 based on the temperature values also shown in FIG. 7. In this regard, plot 750 shows R-Values determined for area 138A of wall surface 138 and plot 760 shows R-Values determined for area 138B of wall surface 138.

Upon inspection of FIG. 7, it will be appreciated that the R-Values of plots 750 and 760 exhibit various fluctuations until a steady state heat flow condition is achieved. In this regard, prior to approximately 11:16 AM, air temperature Tair2 of environment 190 (plot 720) varies greatly which results in corresponding fluctuations in plots 750 and 760. However, after approximately 11:16 AM, the variations in air temperature Tair2 are reduced which result in a heat flow approximating a steady state condition. This results in more consistent calculated R-Values as shown in FIG. 7. Thus, it will be appreciated that it is preferable to use infrared images captured during steady state heat flow conditions during the process of FIG. 6.

The following Table 1 identifies various statistics determined for areas 138A and 138B of wall surface 138 using temperatures obtained during time periods 780 and 790 shown in FIG. 7:

TABLE 1

| | Time Period | | | Statistics | | |
|---|---|---|---|---|---|---|
| No. | Start | End | Area | R-Value | Standard Deviation | Uncertainty |
| 780 | Jul. 11, 2008 9:43 AM | Jul. 11, 2008 2:31 PM | 138A | 13.1 | 1.65 | 12.6% |
| 790 | Jul. 11, 2008 11:16 AM | Jul. 11, 2008 2:31 PM | 138A | 12.3 | 0.66 | 5.3% |
| 780 | Jul. 11, 2008 9:43 AM | Jul. 11, 2008 2:31 PM | 138B | 3.5 | 0.10 | 2.8% |
| 790 | Jul. 11, 2008 11:16 AM | Jul. 11, 2008 2:31 PM | 138B | 3.4 | 0.06 | 1.8% |

In Table 1, the uncertainty values are determined by the ratio of the standard deviation to the average R-Value for each time period. Upon inspection of the temperature values shown in FIG. 7, it will be appreciated that the heat flow occurring during time period 790 approximates a steady state condition better than time period 780. As such, time period 790 exhibits a smaller standard deviation and reduced uncertainty in the R-Values calculated for both of areas 138A and 138B of wall surface 138 as shown in Table 1. In one embodiment, camera 110 and/or computing device 114 may be configured to identify (e.g., select) one or more calculated R-Values corresponding to approximately steady state heat flow conditions.

Figure 8:
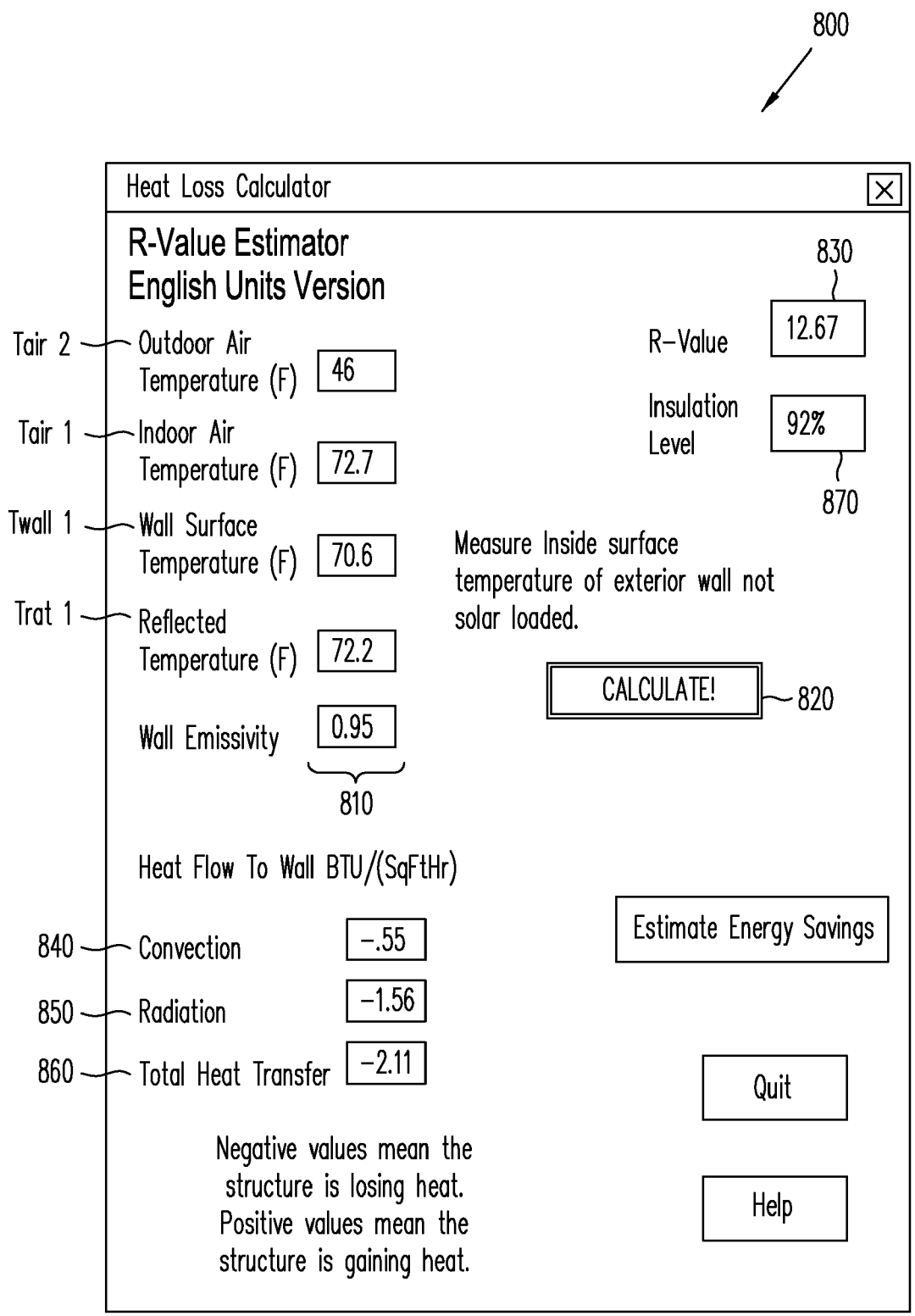
FIG. 8 illustrates an example of a user interface which may be used to calculate an R-Value of the wall of FIG. 1 in accordance with an embodiment of the invention.

In various embodiments, camera 110 and/or computing device 114 may provide a user interface 800 shown in FIG. 8 during step 645. In one embodiment, a user may provide values to input fields 810. In another embodiment, camera 110, and/or computing device 114 may provide values to input fields 810 without requiring user intervention.

As identified in FIG. 8, user interface 800 includes a plurality of input fields 810 to receive temperature values Tair1, Tair2, Twall1, and Trat1 (e.g., determined by camera 110 and/or computing device 114 in previous step 640), as well as an emissivity value for wall 130. It will be appreciated that any emissivity values may be used that are appropriate for wall 130. For example, in one embodiment, an emissivity value of 0.95 corresponding to conventional painted drywall may be used.

After the various values are provided to input fields 810, camera 110 and/or computing device 114 may calculate an R-Value in accordance with the various techniques described herein. In one embodiment, a user may trigger the calculation by selecting an execution button 820. In another embodiment, camera 110 and/or computing device 114 may trigger the calculation.

Also in step 645, camera 110 and/or computing device 114 may calculate values for convective heat Qconv, radiant heat Qrad, and total heat transfer (e.g., the sum of Qconv and Qrad) in accordance with techniques described herein.

Also in step 645, camera 110 and/or computing device 114 may calculate an insulation level IL corresponding to a ratio of the temperature drop across the building envelope of structure 160 from wall surface 138 to environment 190, to the total temperature drop between environment 180 and environment 190. For example, in one embodiment, the insulation level IL can be determined in accordance with the following equation 14:

$$IL = \frac{Twall_1 - Tair_2}{Tair_1 - Tair_2} \quad \text{(equation 14)}$$

In step 650, camera 110 and/or computing device 114 displays the R-Value calculated in step 645 to a user. For example, in one embodiment, the calculated R-Value may be displayed in an output field 830 shown in user interface 800. Also in step 650, values for convective heat Qconv, radiant heat Qrad, total heat transfer, and insulation level may be displayed in output fields 840, 850, and 860, and 870, respectively, of user interface 800.

In step 655, camera 110 and/or computing device 114 calculates various estimated energy costs and energy cost savings based on estimated adjustments to the R-Value of wall 130. For example, in one embodiment, camera 110 and/or computing device 114 may provide a user interface during step 655, such as user interface 900 shown in FIG. 9.

Figure 9:
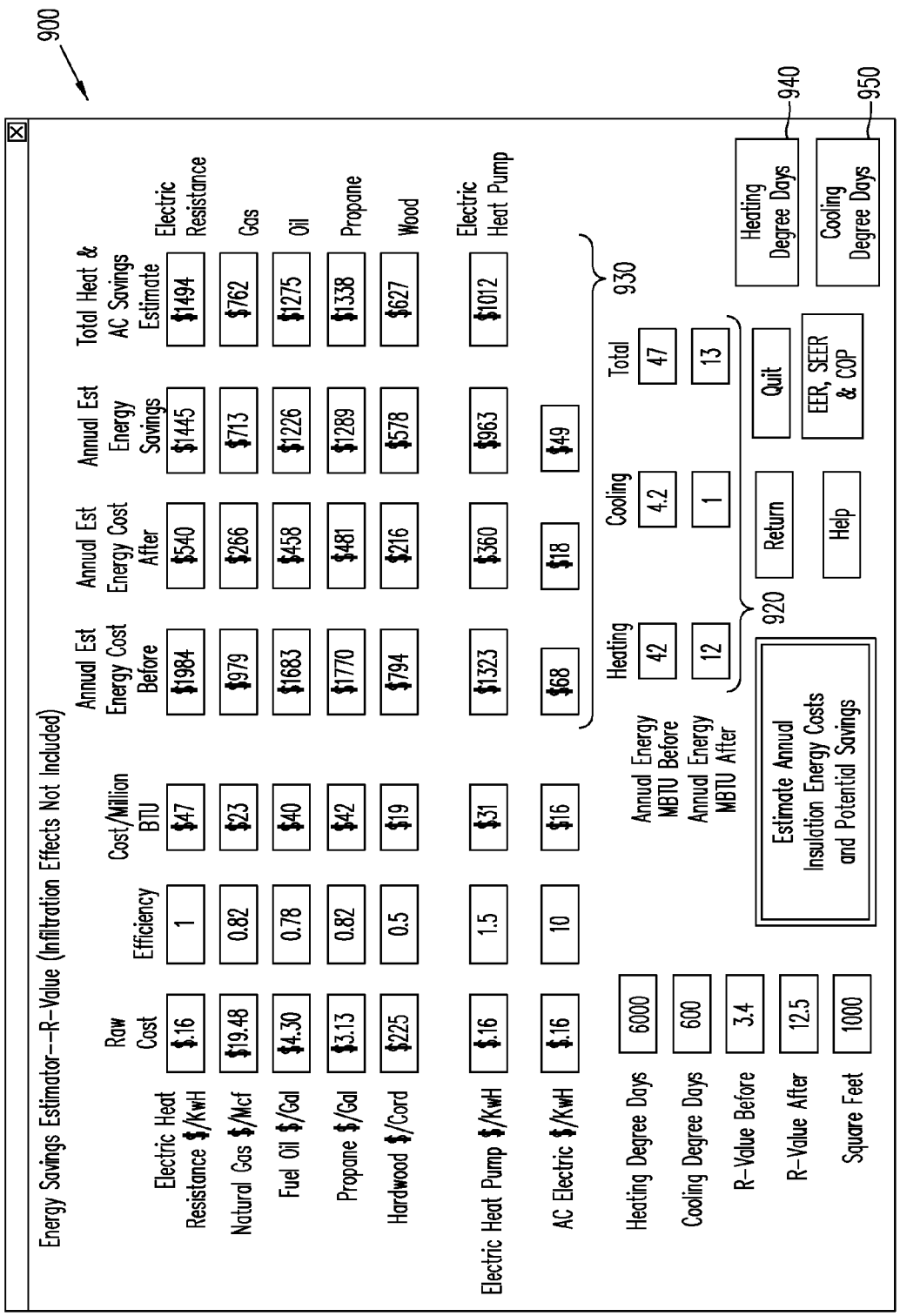
FIG. 9 illustrates an example of a user interface which may be used to calculate cost savings associated with adjusting the R-Value of the wall of FIG. 1 in accordance with an embodiment of the invention.

As identified in FIG. 9, user interface 900 includes a plurality of input fields 910 to receive various raw costs and efficiency values associated with various energy sources. Input fields 910 may also receive a coefficient of performance (COP) for an electric heat pump source, and an energy efficiency ratio (EER) for an alternating current electric heat source. Input fields 910 may further receive a square footage value (e.g., the square footage of structure 160).

In addition, input fields 910 may receive an initial R-Value (labeled "R-Value Before") and an adjusted R-Value (labeled "R-Value After"). In one embodiment, the initial R-Value may be the R-Value of wall 130 calculated in step 645 in accordance with techniques described herein, and the adjusted R-Value may be an estimated new R-Value of wall 130 that a user may wish to implement in wall 130 by modifying insulation 134 or other materials of wall 130.

Input fields 910 may also receive values for heating degree days and cooling degree days. As will be appreciated by those skilled in the art, such degree day values correspond to the difference between the average outdoor temperature and a predefined base temperature (for example, 65 degrees F.) for a 24 hour period. For example, in one embodiment, degree day values can be obtained for various cities and regions of the United States from the National Oceanic and Atmospheric Administration (NOAA) by selecting buttons 940 and 950 of user interface 900.

When calculating energy costs, energy used over time can be determined by rewriting equation 1 and multiplying by time t (in hours) to obtain the following equation 15:

$$E = Qt = \frac{A\Delta T_{io}t}{R - \text{Value}} \text{ in BTU} \quad \text{(equation 15)}$$

In one embodiment, a heating or cooling degree day value (labeled "DegDay") as described herein may be substituted for $\Delta Tio*t$ into equation 15 and multiplied by 24 hours to provide the following equation 16:

$$E = Qt = \frac{24A DegDay}{R - \text{Value}} \text{ in BTU} \quad \text{(equation 16)}$$

Thus, by identifying heating degree days (e.g., winter days) and cooling degree days (e.g., summer days) in input fields 910, camera 110 and/or computing device 114 can calculate estimated energy lost through a particular area A having a given R-Value for heating and cooling. Also, based on these energy lost estimates, camera 110 and/or computing device 114 can determine estimated energy costs and energy cost savings associated with an adjusted R-Value.

In step 660, camera 110 and/or computing device 114 displays the various estimated energy costs and energy cost savings calculated in step 655 to a user. For example, in one embodiment, such values may be displayed in fields 920 and 930 of user interface 900. In another embodiment, camera 110 and/or computing device 114 may display portions of user interface 900 for specific fuel types (e.g., natural gas, electric air conditions, and/or other fuel types) including the estimated energy costs and/or energy cost savings determined for such fuel types.

Although the process of FIG. 6 has been described as using infrared images captured by camera 110, other approaches are also contemplated. In one embodiment, some of the temperatures described herein may be determined based on infrared images taken by camera 110, while other temperatures may be determined based on temperature measurements by another appropriate measuring device in environment 180 and/or environment 190. For example, camera 110 may be used to capture infrared images only in environment 180, and air temperature Tair2 of environment 190 may be measured using another appropriate measuring device.

It will be appreciated that the R-Value associated with wall 130 has been described as including R-Values attributable to the combination of wall 130, internal air film 140, and external air film 150. However, in another embodiment, the effects of internal air film 140 and external air film 150 may be removed to determine the R-Value attributable to only wall 130. In this regard, the surface temperatures of both of wall surfaces 138 and 139 may be determined from thermal images of wall surfaces 138 and 139 captured by camera 110. For example, camera 110 may be positioned in environment 180 to capture a thermal image of wall surface 138, and then repositioned in environment 190 to capture a thermal image of wall surface 139. Using these the wall surface temperatures determined from such thermal images, the separate R-Values attributable to internal air film 140 and external air film 150 may be determined in accordance with the techniques described herein. As a result, the R-Value attributable to wall 130 itself may be determined by subtracting the R-Values attributable to internal air film 140 and external air film 150 from the total R-Value identified in equation 1.

In view of the present disclosure, it will be appreciated that various techniques described herein may be used to determine R-Values associated with walls in contact with various indoor and/or outdoor environments. In particular, by using an infrared camera to determine temperatures from a plurality of surfaces shown in a thermal image, R-Values may be determined with high accuracy, especially during steady state heat flow conditions. Advantageously, after the R-Value for a wall has been determined, cost savings associated with other adjusted R-Values may also be determined. As a result, a user can efficiently determine the approximate cost savings associated with changes in building materials which in turn affect the R-Values.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as program code and/or data, can be stored on one or more machine readable mediums (e.g., computer readable media or other mediums). It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the present invention. Accordingly, the scope of the invention is defined only by the following claims.

What is claimed is:

1. A method of determining thermal resistance associated with a wall, the method comprising:
   capturing an infrared image comprising a surface of the wall and a surface of at least one target using an infrared camera, wherein the wall surface and the target are in a first environment on a first side of the wall, and wherein the target surface is a substantially reflective surface;
   determining a temperature of the wall surface from the infrared image;
   determining a temperature of the target surface from the infrared image, wherein the target surface temperature corresponds to a reflected apparent temperature of the first environment;
   determining a temperature of a second environment on a second side of the wall; and
   calculating a thermal resistance value of the wall based on the wall surface temperature, the target surface temperature, and the temperature of the second environment.

2. The method of claim 1, wherein the target is at approximately thermal equilibrium with the first environment during the capturing.

3. The method of claim 1, wherein the target is a first target, wherein the infrared image further comprises a surface of a second target in the first environment, the method further comprising determining a temperature of the second target surface from the infrared image, wherein the second target surface is a substantially non-reflective surface, wherein the temperature of the second target surface corresponds to a temperature of air of the first environment, wherein the calculated thermal resistance value is further based on the second target surface temperature.

4. The method of claim 1, wherein the infrared image is a first infrared image, the method further comprising capturing a second infrared image in the second environment, wherein the second environment temperature is determined from the second infrared image.

5. The method of claim 1, wherein the determining and calculating steps are performed by the infrared camera.

6. The method of claim 1, wherein the determining and calculating steps are performed by a computing device.

7. The method of claim 1, further comprising:
calculating energy costs associated with the calculated thermal resistance value and an adjusted thermal resistance value; and
calculating a cost savings based on the calculated energy costs.

8. The method of claim 1, further comprising repeating the method to determine a plurality of thermal resistance values.

9. The method of claim 1, wherein the thermal resistance value is associated with radiative and convective heat flow through the wall.

10. The method of claim 1, wherein the thermal resistance value corresponds to an approximately steady state heat flow through the wall.

11. The method of claim 1, wherein the thermal resistance value associated with the wall is attributable to a combination of the wall, a first air film adjacent to the first side of the wall, and a second air film adjacent to the second side of the wall.

12. The method of claim 1, wherein the thermal resistance value associated with the wall is attributable to only the wall itself.

13. The method of claim 1, wherein the thermal resistance value is an R-Value.

14. A system for determining thermal resistance associated with a wall, the system comprising:
an infrared camera adapted to:
capture an infrared image comprising a surface of the wall and a surface of at least one target, wherein the wall surface and the target are in a first environment on a first side of the wall, and wherein the target surface is a substantially reflective surface,
determine a temperature of the wall surface from the infrared image, and
determine a temperature of the target surface from the infrared image, wherein the target surface temperature corresponds to a reflected apparent temperature of the first environment; and
a processor configured to calculate a thermal resistance value of the wall based on the wall surface temperature, the target surface temperature, and a temperature of a second environment on a second side of the wall.

15. The system of claim 14, wherein the processor is part of the infrared camera.

16. The system of claim 14, wherein the processor is part of a computing system.

17. The system of claim 14, wherein the system further comprises a measuring device adapted to be positioned in the second environment to measure the second environment temperature.

18. The system of claim 14, wherein the infrared image is a first infrared image, wherein the infrared camera is adapted to capture a second infrared image in the second environment and determine the second environment temperature from the second infrared image.

19. The system of claim 14, wherein the processor is adapted to:
calculate energy costs associated with the calculated thermal resistance value and an adjusted thermal resistance value; and
calculate a cost savings based on the calculated energy costs.

20. The system of claim 14, wherein the infrared camera is adapted to provide a user interface to instruct a user to position the target and initiate the capture of the thermal image.

21. The system of claim 14, wherein the infrared camera is adapted to capture a plurality of infrared images comprising the wall surface and the target surface and determine temperatures of the wall surface and the target surface from the infrared images, wherein the processor is configured to calculate a plurality of thermal resistance values based on the wall surface temperatures, the target surface temperatures, and the temperature of the second environment.

22. The system of claim 14, wherein the thermal resistance value is associated with radiative and convective heat flow through the wall.

23. The system of claim 14, wherein the thermal resistance value corresponds to an approximately steady state heat flow through the wall.

24. The system of claim 14, wherein the infrared camera comprises a range finder adapted to determine a distance from the infrared camera to the wall surface, wherein the thermal resistance value is further based on the distance determined by the range finder.

25. The system of claim 14, wherein the thermal resistance value associated with the wall is attributable to a combination of the wall, a first air film adjacent to the first side of the wall, and a second air film adjacent to the second side of the wall.

26. The system of claim 14, wherein the thermal resistance value associated with the wall is attributable to only the wall itself.

27. The system of claim 14, wherein the thermal resistance value is an R-Value.

28. A non-transitory machine-readable medium comprising a plurality of machine-readable instructions which when executed by a device are adapted to cause the device to perform a method of determining thermal resistance associated with a wall, the method comprising:
instructing a user to operate an infrared camera to capture an infrared image comprising a surface of the wall and a surface of at least one target, wherein the wall surface and the target are in a first environment on a first side of the wall, and wherein the target surface is a substantially reflective surface;
instructing a user to measure a temperature of a second environment on a second side of the wall;
determining a temperature of the wall surface from the infrared image;
determining a temperature of the target surface from the infrared image, wherein the target surface temperature corresponds to a reflected apparent temperature of the first environment; and calculating a thermal resistance value of the wall based on the wall surface temperature, the target surface temperature, and the temperature of the second environment.

29. The non-transitory machine-readable medium of claim 28, wherein the device is the infrared camera.

30. The non-transitory machine-readable medium of claim 28, wherein the device is a computing device.

31. The non-transitory machine-readable medium of claim 28, wherein the infrared image is a first infrared image, wherein the instructing a user to measure a temperature of a second environment comprises instructing the user to capture a second infrared image in the second environment, wherein the method further comprises determining the temperature of the second environment from the second infrared image.

32. The non-transitory machine-readable medium of claim 28, wherein the method further comprises:
   receiving an adjusted thermal resistance value;
   calculating energy costs associated with the calculated thermal resistance value and the adjusted thermal resistance value; and
   calculating a cost savings based on the calculated energy costs.

33. The non-transitory machine-readable medium of claim 28, wherein the method further comprises repeating the method to determine a plurality of thermal resistance values.

34. The non-transitory machine-readable medium of claim 28, wherein the thermal resistance value is associated with radiative and convective heat flow through the wall.

35. The non-transitory machine-readable medium of claim 28, wherein the thermal resistance value corresponds to an approximately steady state heat flow through the wall.

36. The non-transitory machine-readable medium of claim 28, wherein the thermal resistance value associated with the wall is attributable to a combination of the wall, a first air film adjacent to the first side of the wall, and a second air film adjacent to the second side of the wall.

37. The non-transitory machine-readable medium of claim 28, wherein the thermal resistance value associated with the wall is attributable to only the wall itself.

38. The non-transitory machine-readable medium of claim 28, wherein the thermal resistance value is an R-Value.

* * * * *